United States Patent
Wang et al.

(10) Patent No.: US 11,112,398 B2
(45) Date of Patent: Sep. 7, 2021

(54) APPARATUS AND METHOD FOR DETERMINING VOLUME STABILITY OF WELL CEMENT

(71) Applicant: PetroChina Company Limited, Beijing (CN)

(72) Inventors: Fuyun Wang, Beijing (CN); Youzhi Zheng, Beijing (CN); Jie Li, Beijing (CN); Huiyun Ma, Beijing (CN); Libin Jiao, Beijing (CN); Tao Yang, Beijing (CN); Jiang Yu, Beijing (CN); Qiyan Tan, Beijing (CN)

(73) Assignee: PetroChina Company Limited, Beijing (CN)

(*) Notice: Subject to any disclaimer, the term of this patent is extended or adjusted under 35 U.S.C. 154(b) by 245 days.

(21) Appl. No.: 16/207,055

(22) Filed: Nov. 30, 2018

(65) Prior Publication Data
US 2019/0302092 A1    Oct. 3, 2019

(30) Foreign Application Priority Data
Apr. 2, 2018    (CN) .......................... 201810281222.3

(51) Int. Cl.
*G01N 33/38*    (2006.01)
*G01N 3/18*    (2006.01)
(Continued)

(52) U.S. Cl.
CPC ......... *G01N 33/383* (2013.01); *E21B 47/005* (2020.05); *G01N 3/18* (2013.01); *E21B 33/14* (2013.01)

(58) Field of Classification Search
CPC ........ E21B 33/14; E21B 47/005; E21B 33/13; E21B 33/16; E21B 27/02; E21B 33/05;
(Continued)

(56) References Cited

U.S. PATENT DOCUMENTS

| 4,928,269 A * | 5/1990 | Kimball ................. G01V 1/306 |
| | | 181/105 |
| 7,191,663 B2 * | 3/2007 | Go Boncan .............. G01N 3/08 |
| | | 73/803 |

(Continued)

FOREIGN PATENT DOCUMENTS

| CN | 102928578 A | 2/2013 |
| CN | 103184866 A | 7/2013 |

(Continued)

OTHER PUBLICATIONS

Li, Study of the failure mechanisms of a cement sheath based on an equivalent physical experiment, 2016 (Year: 2016).*

(Continued)

*Primary Examiner* — John Fitzgerald
*Assistant Examiner* — Truong D Phan
(74) *Attorney, Agent, or Firm* — Foley & Lardner LLP (57) ABSTRACT

An apparatus and method for determining a volume stability of well cement including a reaction kettle, a radial contraction, an expansion ring, a heater, a pressurizer, and a volume change parameter tester. The radial contraction and expansion ring include a first casing and a second casing, the first casing is a casing made of elastic material, the second casing is a steel casing, and the first casing sheathes the second casing. The heater and the pressurizer are used to provide a preset temperature and a preset pressure respectively and the volume change parameter tester is used to detect a radial volume change parameter of the well cement. The apparatus is provided with the radial contraction and expansion ring to acquire the radial volume change parameter of the well cement, and comprehensively evaluates the volume stability of the well cement using the radial volume change parameter of the well cement.

10 Claims, 5 Drawing Sheets

(51) Int. Cl.
*E21B 33/14* (2006.01)
*E21B 47/005* (2012.01)

(58) Field of Classification Search
CPC .... E21B 33/134; E21B 33/146; E21B 33/165; E21B 33/167; E21B 43/261; G01N 33/383; G01N 3/08; G01N 3/12; G01N 3/18; G01N 33/38; G01N 2291/0232; G01N 3/28
See application file for complete search history.

(56) References Cited

U.S. PATENT DOCUMENTS

| | | | | |
|---|---|---|---|---|
| 7,621,186 | B2* | 11/2009 | Heathman | G01N 3/24 73/803 |
| 8,794,078 | B2* | 8/2014 | Darbe | G01N 3/10 73/803 |
| 9,067,825 | B2* | 6/2015 | Bullerjahn | C04B 40/0039 |
| 2005/0080161 | A1* | 4/2005 | Tare | C09K 8/50 523/130 |
| 2005/0126300 | A1* | 6/2005 | Go Boncan | G01N 3/08 73/803 |
| 2005/0152432 | A1* | 7/2005 | Hakimuddin | G01N 33/383 374/53 |
| 2011/0094295 | A1* | 4/2011 | Meadows | G01N 3/12 73/38 |
| 2013/0228019 | A1* | 9/2013 | Meadows | G01N 3/08 73/821 |
| 2013/0340505 | A1* | 12/2013 | Go Boncan | G01N 33/383 73/38 |
| 2014/0174192 | A1* | 6/2014 | Shine, Jr. | G01N 33/383 73/803 |
| 2016/0032706 | A1* | 2/2016 | Bornaz | C09K 8/467 166/250.01 |
| 2017/0096874 | A1* | 4/2017 | Parsons | E21B 33/14 |
| 2017/0205388 | A1* | 7/2017 | Thomas | G01N 33/383 |
| 2018/0058174 | A1* | 3/2018 | Yue | E21B 33/1204 |

FOREIGN PATENT DOCUMENTS

| | | |
|---|---|---|
| CN | 103245773 A | 8/2013 |
| CN | 103558364 A | 2/2014 |
| CN | 104153760 | 11/2014 |
| CN | 104153960 A | 11/2014 |
| CN | 106771096 A | 5/2017 |
| CN | 106991235 A | 7/2017 |
| CN | 107064471 A | 8/2017 |
| CN | 107167396 A | 9/2017 |
| CN | 107561251 A | 1/2018 |
| KR | 10-1337548 B1 | 11/2013 |

OTHER PUBLICATIONS

Du et al., "Study on the Impact of High and Low Calcium Fly Ash on Concrete Block Volume Stability," Zhejiang Construction, vol. 30, pp. 58-63 (Nov. 2013).
Chinese Office Action and Search Report, App. No. 201810281222.3 (dated Oct. 30, 2019).

* cited by examiner

APPARATUS AND METHOD FOR DETERMINING VOLUME STABILITY OF WELL CEMENT

CROSS-REFERENCE TO RELATED PATENT APPLICATIONS

This application claims the benefit of and priority to Chinese Application No. 2018102812223, filed Apr. 2, 2018, which is incorporated herein by reference in its entirety.

TECHNICAL FIELD

The present application relates to the technical field of oil and gas development, and in particular to an apparatus and method for determining a volume stability of well cement.

BACKGROUND

During the oil and gas well deployment, cement is usually injected into an annulus between the formation and a casing to form a cement ring for well cementation. However, the expansion and contraction of the volume of the cement ring formed during and after the solidification process of the cement may influence the cementing quality. Therefore, it is very important to determine the volume stability of the well cement in advance and to thereby choose a well cement ring with a relatively-high volume stability.

At present, most of existing methods simply use a reaction kettle to test the axial stability of the cement sample, and evaluate the volume stability of the well cement only by taking the axial stability as an index parameter, so that when the existing methods are implemented, there is often a technical problem that the determination of the volume stability of the well cement is not comprehensive and the accuracy thereof is poor.

Regarding the above technical problem, no effective solution has been proposed yet.

SUMMARY

The embodiments of the present application provide an apparatus and method for determining a volume stability of well cement, so as to solve the technical problem of the existing methods that the determination of the volume stability of the well cement is not comprehensive and the accuracy thereof is poor, and achieve the technical effect of more accurately and comprehensively evaluating the volume stability of the well cement by detecting and utilizing a radial volume change parameter of the well cement.

The embodiments of the present application provide an apparatus for determining a volume stability of well cement including a reaction kettle, a radial contraction and expansion ring, a heater, a pressurizer, and a volume change parameter tester, where the radial contraction and expansion ring includes a first casing and a second casing, the first casing is a casing made of elastic material, the second casing is a steel casing; the first casing sheathes the second casing, an upper cover and a lower cover are provided at a top and a bottom of the radial contraction and expansion ring, respectively, and an annulus between the first casing and the second casing accommodates a well cement sample of a target area to be detected; the radial contraction and expansion ring is provided in the reaction kettle; the heater is connected to the reaction kettle, and is used to provide a preset temperature to the radial contraction and expansion ring; the pressurizer is connected to the reaction kettle, and is used to provide a preset pressure to the radial contraction and expansion ring; and the volume change parameter tester is connected to the reaction kettle, and is used to determine a radial volume change parameter of the well cement by detecting a deformation parameter of the second casing under a condition of the preset temperature and the preset pressure, the radial volume change parameter is used to determine the volume stability of the well cement and represent a radial volume change rate of the well cement sample.

In one embodiment, a rubber seal is achieved between the radial contraction and expansion ring and the upper cover, and a rubber seal is achieved between the radial contraction and expansion ring and the lower cover.

In one embodiment, an injection hole and a discharge hole are provided on the upper cover, the injection hole is communicated with the annulus between the first casing and the second casing, and the discharge hole is communicated with the annulus between the first casing and the second casing.

In one embodiment, a pressure adjusting holes is provided on the upper cover and the lower cover, respectively, and is communicated with an interior of the second casing.

In one embodiment, a fixing hole is provided at a center position of the lower cover, and is used to fix the radial contraction and expansion ring in the reaction kettle.

In one embodiment, the apparatus further includes a processor connected to the volume change parameter tester and used to determine the volume stability of the well cement according to the radial volume change parameter of the well cement and the axial volume change parameter of the well cement, the axial volume change parameter of the well cement represents an axial volume change rate of the well cement.

The embodiments of the present application further provide a method for determining a volume stability of well cement, including acquiring a well cement sample of a target area;

testing, by an apparatus for determining a volume stability of well cement, a radial volume change of the well cement sample under a condition of a preset temperature and a preset pressure, to acquire a radial volume change parameter of the well cement;

testing an axial volume change of the well cement sample under the condition of the preset temperature and the preset pressure, to acquire an axial volume change parameter of the well cement; and determining the volume stability of the well cement according to the radial volume change parameter of the well cement and the axial volume change parameter of the well cement.

In one embodiment, the preset temperature is determined according to a downhole temperature of the target area, and the preset pressure is determined according to a downhole pressure of the target area.

In one embodiment, determining the volume stability of the well cement according to the radial volume change parameter of the well cement and the axial volume change parameter of the well cement includes comparing the radial volume change parameter of the well cement with a radial volume change threshold, and comparing the axial volume change parameter of the well cement with an axial volume change threshold, and when the radial volume change parameter of the well cement is smaller than the radial volume change threshold and the axial volume change parameter of the well cement is smaller than the axial volume change threshold, determining that the volume stability of the well cement is satisfactory.

In one embodiment, the well cement sample includes cements of a plurality of ratios for constructing a cement ring between a downhole formation and a downhole casing in the target area.

In the embodiments of the present application, the volume stability of the well cement is comprehensively evaluated by detecting a radial volume change parameter of the well cement by means of the disposed radial contraction and expansion ring so as to introduce the radial volume change parameter of the well cement in consideration of actual volume change characteristics of the downhole cement ring, thereby solving the technical problem of the existing methods that the determination of the volume stability of the well cement is not comprehensive and the accuracy thereof is poor, and achieving the technical effect of more accurately and comprehensively evaluating the volume stability of the well cement by detecting and utilizing the radial volume change parameter of the well cement.

BRIEF DESCRIPTION OF THE DRAWINGS

In order to more clearly describe the technical solutions in the embodiments of the present application or in the prior art, the drawings to be used in the descriptions of the embodiments or the prior art will be briefly introduced as follows. Obviously, the drawings in the following descriptions just illustrate some embodiments of the present application, and those skilled in the art can obtain other drawings from these drawings without paying any creative effort.

Reference numerals: 1: reaction kettle; 2: radial contraction and expansion ring; 21: upper cover; 22: lower cover; 23: first casing; 24: second casing; 3: heater; 4: pressurizer; 5: volume change parameter tester.

DETAILED DESCRIPTION

In order that those skilled in the art can better understand the technical solutions of the present application, the technical solutions in the embodiments of the present application will be clearly and completely described as follows with reference to the drawings of the embodiments of the present application. Obviously, those described herein are just a part, rather than all, of the embodiments of the present application. Any other embodiment obtained by those skilled in the art based on the embodiments of the present application without paying any creative labor should fall within the protection scope of the present application.

When determining the volume stability of the well cement, the existing methods only consider the influence on the cementing quality of the axial volume change of the well cement, without comprehensively analyzing the volume change characteristics of the well cement in the actual construction scene, and thus evaluates the volume stability of the well cement only by testing and utilizing the radial volume change parameter as an index parameter, so that when the existing methods are implemented, there is often a technical problem that the determination of the volume stability of the well cement is not comprehensive and the accuracy thereof is poor. In fact, the radial volume change of the downhole well cement ring also has a significant influence on the cementing quality. For example, the radial volume expansion of the cement ring squeezes the casing and even leads to a cementation failure in severe cases; while the radial volume contraction of the cement ring causes a bonding quality defect at an interface between the cement ring and the casing, and even produces micro-gaps which form annulus fluid channeling, thereby causing a loss of the oil and gas resources or a damage to the reservoirs. However, the existing methods do not consider the influence on the cementing quality of the radial volume change of the well cement, and there is also no special apparatus for measuring the radial volume change parameter of the well cement. In view of the above problems, the present application comprehensively evaluates the volume stability of the cement by disposing radial contraction and expansion ring to detect a radial volume change parameter of the cement and then introducing the radial volume change parameter of the cement in consideration of actual volume change characteristics of the downhole cement ring, thereby solving the technical problem of the existing methods that the determination of the volume stability of the well cement is not comprehensive and the accuracy thereof is poor, and achieving the technical effect of more accurately and comprehensively evaluating the volume stability of the well cement by detecting and utilizing the radial volume change parameter of the well cement.

Figure 1:
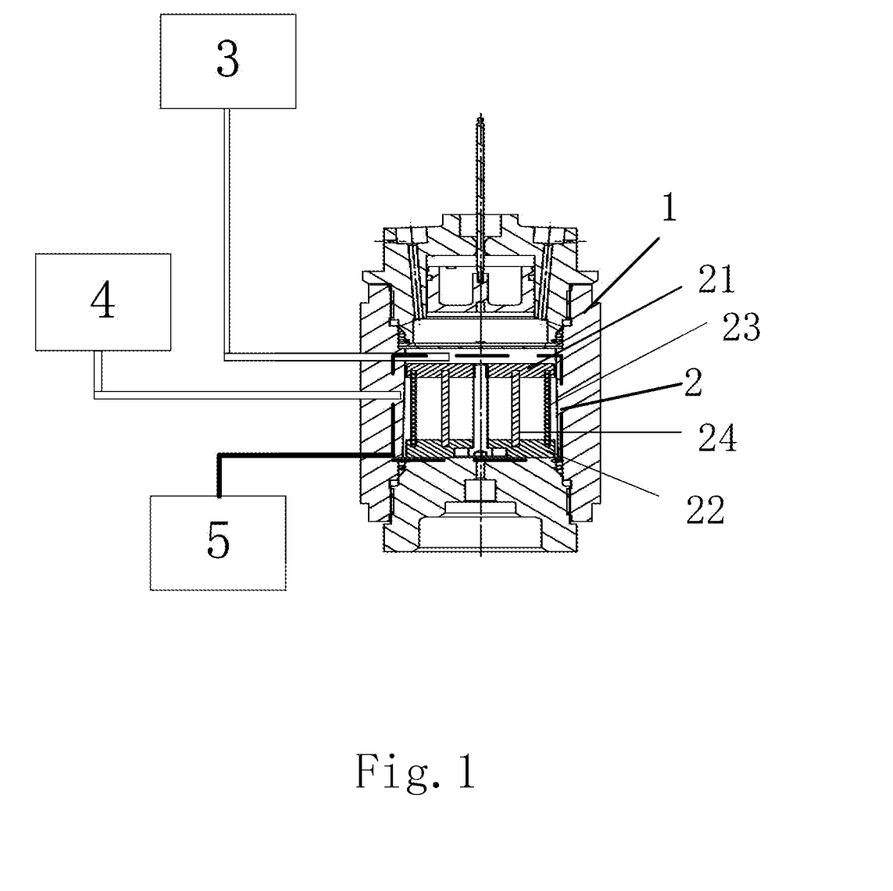
FIG. 1 is a schematic structural diagram of an apparatus for determining a volume stability of well cement provided by an embodiment of the present application.

Based on the above idea, the embodiments of the present application provide an apparatus for determining a volume stability of well cement. For the detail, please refer to the schematic structural diagram of an apparatus for determining a volume stability of well cement provided by an embodiment of the present application as illustrated in FIG. 1. An apparatus for determining a volume stability of well cement provided by an embodiment of the present application specifically may include a reaction kettle 1, a radial contraction and expansion ring 2, a heater 3, a pressurizer 4 and a volume change parameter tester 5, wherein the radial contraction and expansion ring 2 specifically may include a first casing 23 and a second casing 24; the first casing 23 specifically may be a casing made of elastic material, and the second casing 24 specifically may be a steel casing; the first casing 23 specifically may sleeve the second casing 24; an upper cover 21 and a lower cover 22 are provided at a top and a bottom of the radial contraction and expansion ring 2, respectively; an annulus between the first casing 23 and the second casing 24 accommodates a well cement sample of a target area to be detected; the radial contraction and expansion ring 2 specifically may be provided in the reaction kettle 1; the heater 3 specifically may be connected to the reaction kettle 1, and used to provide a preset temperature to the radial contraction and expansion ring 2; while the pressurizer 4 specifically may be connected to the reaction kettle 1, and used to provide a preset pressure to the radial contraction and expansion ring 2; and the volume change parameter tester 5 specifically may be connected to the reaction kettle 1, and be used to determine a radial volume change parameter of the well cement by detecting a deformation parameter of the second casing 24 under the preset temperature and the preset pressure, and the radial volume change parameter specifically may be used to determine the volume stability of the well cement, wherein the radial volume change parameter represents a radial volume change rate of the well cement sample.

In this embodiment, the first casing 23 is specifically a casing made of an elastic material. Thus, the wall of the first casing 23 has a certain expansibility and contractility, and then can be deformed correspondingly along with the volume change of the cement in the annulus between the first casing 23 and the second casing 24. Specifically, the first casing 23 may be a rubber casing. By using the rubber casing as the first casing 23, it is possible to accurately simulate a relatively soft formation interface in contact with the well cement ring under an actual construction environment. Of course, it should be noted that using the rubber casing as the first casing listed above is only a schematic illustration. During implementation, it is also possible to use any other suitable elastic material to manufacture the first casing according to the specific conditions and construction requirements, which is not limited herein. The structure and usage of the apparatus for determining the volume stability of the well cement is described below through an example in which the rubber casing is used as the first casing.

In this embodiment, it should be emphasized that the existing methods only consider the axial volume instability of the well cement ring, like the influence on the cementing quality of the axial expansion or contraction of the cement ring, and then only acquires and uses the axial volume change parameter of the well cement as a unique index parameter to evaluate the volume stability of the well cement. In fact, under the specific construction environment, the volume of the cement ring for well cementation will also change in the radial direction due to the characteristics of the cement itself, e.g., there may be expansion or contraction in the radial direction, and the radial volume change of the cement ring also has an obvious influence on the cementing quality. For example, the radial volume expansion of the cement ring squeezes the downhole casing and even leads to a cementation failure in severe cases; while the radial volume contraction of the cement ring causes a bonding quality defect at an interface between the cement ring and the casing, and even produces micro-gaps which form annulus fluid channeling, thereby causing a loss of the oil and gas resources or a damage to the reservoirs. In conjunction with the specific construction scenes and through careful analyses, it is found that during implementation, the existing methods neglect the above problem, resulting in a relatively large error when determining the stability of the well cement. Thus, in order to better evaluate the stability of the well cement ring, it is proposed to comprehensively evaluate the volume stability of the well cement by acquiring the radial volume change parameter of the well cement and then combining the radial volume change parameter, thereby increasing the accuracy of the determined volume stability of the well cement.

In this embodiment, the axial volume change parameter and the radial volume change parameter specifically may be understood as percentages of volume change amounts of the cement after expansions or contractions in axial and radial directions relative to a volume of the cement before the change respectively (i.e., an axial volume change rate and a radial volume change rate). Specifically, for example, the radial volume change parameter of 2.3% may indicate that the cement has expanded radially, and a ratio of a volume increment after the expansion to the original volume is 2.3%. For another example, the axial volume change parameter of −0.9% may indicate that the cement has contracted axially, and a ratio of a volume decrement after the contraction to the original volume is 0.9%. Generally, under the environment of a certain temperature or a certain pressure, as the absolute value of the axial volume change parameter increases, the axial volume change of the cement under the environment increases, and the axial volume stability gets poorer. Similarly, under the environment of a certain temperature or a certain pressure, as the absolute value of the radial volume change parameter increases, the radial volume change of the cement under the environment increases, and the radial volume stability gets poorer.

In one embodiment, it is considered that when the axial volume change parameter of the cement is measured with the existing device, usually the cement slurry for well cementation to be detected is injected into the reaction kettle, and then the axial volume change of the cement in the reaction kettle is measured with a volume parameter tester so as to determine corresponding axial volume change parameter. Since a direct injection of the cement to be detected into the reaction kettle is restricted by the wall of the reaction kettle, a radial deformation of the cement usually cannot occur. Thus, it is often impossible to accurately measure the radial volume change parameter of the cement using the existing device. In conjunction with the specific construction scene and in consideration of the radial deformation characteristics of the well cement forming the cement ring, it is designed a radial contraction and expansion ring 2 for specially matching the test of the radial volume change parameter of the cement. Through the radial contraction and expansion ring 2, the cement to be detected can be shaped into a ring, thereby better simulating the actual shape of the well cement in the cementing construction (based on the existing device, the cement can only be shaped into a column in the reaction kettle); meanwhile, in consideration of the actual downhole environment where the well cement ring is located, it is possible to enable the cement ring to be detected to be radially deformed, and realistically simulate different deformation characteristics of the downhole cement ring in different radial directions (including radial directions away from and approaching a center).

In one embodiment, in order to meet the above requirements, the designed radial contraction and expansion ring 2 specifically may include a first casing 23 and a second casing 24, wherein an inner diameter of the first casing 23 is larger than an outer diameter of the second casing 24, and the first casing 23 sheathes the second casing 24 concentrically, so that an annulus can be formed between the first casing 23 and the second casing 24 to accommodate well cement to be detected and the well cement can be shaped into a ring to obtain a cement ring sample similar to the well cement ring. It should be emphasized that in the actual construction scene, the cement is usually injected into the annulus between the formation and the downhole casing to perform well cementation to form the cement ring, i.e., in the actual construction scene, the inner wall and the outer wall of the cement ring contact with different objects. Specifically, the inner wall of the cement ring contacts with the downhole casing, and the outer wall contacts with the formation. Usually, the casing is made of steel and harder than the formation. Thus, under the restriction of the casing, the deformation degree of the inner wall of the cement ring is often smaller than that of the outer wall of the cement ring. Taking notice of the above characteristic and in order to more accurately simulate the radial force-bearing environment of the downhole cement ring, during implementation, a steel casing may be used as the second casing 24 to simulate the downhole casing contacting with the inner wall of the well cement ring in the specific construction; and a rubber casing may be used as the first casing 23 to simulate the formation contacting with the outer wall of the well cement ring. The walls of the rubber casing and the steel casing are made of materials having different hardness, wherein the wall of the rubber casing is relatively softer and its hardness is close to that of the formation, while the wall of the steel casing is relatively harder and its hardness is close to that of the downhole casing. Thus, through the combination of the first casing 23 and the second casing 24, it can more accurately simulate the radial force-bearing environment of the well cement ring in the downhole, so that the cement placed in the annulus between the first casing 23 and the second casing 24 has a larger deformation degree in the radial direction away from the circle center than in the radial direction approaching the circle center. In addition, since the first casing 23 is a rubber casing with certain elasticity, during implementation, the radial volume change parameter of the cement ring can be accurately determined by testing the volume change of the first casing 23. Of course, it should be noted that the rubber casing and the steel casing listed above are just schematic illustrations, rather than improper limitations to the present disclosure. During implementation, the casings made of other suitable materials may be selected as the first casing and the second casing based on the specific condition, which is not limited herein.

In one embodiment, in order to more accurately test the radial volume change parameter of the well cement and prevent the interference caused by the axial volume change of the well cement, during implementation, an upper cover 21 may be provided at a top of the radial contraction and expansion ring 2, and a lower cover 22 may be provided at a bottom of the radial contraction and expansion ring 2, which may restrict the axial volume change of the cement sample, so as to obtain a relatively accurate radial volume change parameter by testing.

In one embodiment, in consideration that in the specific construction, the well cement ring is often under the environment of high temperature and high pressure, and in order to more accurately simulate the environment of the well cement to obtain a truer radial volume change parameter, during implementation, the above apparatus may further include a heater 3 and a pressurizer 4, wherein the heater 3 and the pressurizer 4 can be respectively connected into the reaction kettle 1 through a conduit, so as to heat and pressurize the radial contraction and expansion ring 2 in the reaction kettle 1 according to the environment condition of the target area, and maintain the temperature of the environment where the radial contraction and expansion ring 2 is located at a preset temperature and maintain the pressure of the environment where the radial contraction and expansion ring 2 is located at a preset pressure, so that the temperature and pressure environment for the well cement can be realistically simulated to obtain a more accurate radial volume change parameter. In which, the preset temperature specifically may be determined according to a downhole temperature of the target area, and the preset pressure specifically may be determined according to a downhole pressure of the target area.

In one embodiment, the apparatus specifically may further include a volume change parameter tester 5 which may be connected to the reaction kettle 1. During implementation, the deformation parameter of the first casing 23 can be tested by the volume change parameter tester 5, thereby calculating the radial volume change parameter of the well cement according to the deformation parameter of the first casing 23.

In one embodiment, the volume change parameter tester 5 specifically may be a contraction and expansion analyzer. Specifically, the volume change parameter tester is provided with a sensor. During implementation, a corresponding deformation parameter may be collected by the sensor, so as to determine a corresponding volume change parameter according to the deformation parameter. Of course, the contraction and expansion analyzer listed above is just a schematic illustration. During implementation, any other test device may be selected as the volume change parameter tester based on the specific condition and the construction requirement, which is not limited herein.

Relative to the existing devices, the embodiments of the present application comprehensively evaluate the volume stability of the well cement by detecting a radial volume change parameter of the well cement by means of the disposed radial contraction and expansion ring so as to introduce the radial volume change parameter of the well cement in consideration of the actual volume change characteristics of the downhole cement ring, thereby solving the technical problem of the existing methods that the determination of the volume stability of the well cement is not comprehensive and the accuracy thereof is poor, and achieving the technical effect of more accurately and comprehensively evaluating the volume stability of the well cement by detecting and utilizing the radial volume change parameter of the well cement.

In one embodiment, the first casing 23 specifically may be a rubber casing resistant to the high temperature and corrosion, which can prevent the accuracy of the tested radial volume change parameter from being affected by a large change of the expansibility and contractility of the first casing 23 caused by a corrosion of the rubber casing or a change of the material of the rubber casing under the high-temperature and high-pressure condition, when the radial volume change parameter of the well cement is tested under the preset temperature and the preset pressure. At the same time, the service life of the first casing in the apparatus for determining the volume stability of the well cement can also be prolonged.

In one embodiment, during implementation, the area between the reaction kettle 1 and the radial contraction and expansion ring 2 may be fully injected with liquid such as water, a rubber diaphragm may be provided at a boundary between the reaction kettle 1 and the external, and a test sensor of the volume change parameter tester 5 may be connected to the rubber diaphragm. As a result, when the volume of the cement ring in the radial contraction and expansion ring 2 is changed along the radial direction, the first casing 23 is deformed correspondingly since the cement ring is connected to the first casing 23. In addition, since the space between the radial contraction and expansion ring 2 and the reaction kettle 1 is fully injected with liquid such as water, the above deformation will squeeze the liquid such as water and then be transferred to the rubber diaphragm through the liquid such as water. The volume change parameter tester 5 may determine a deformation parameter of the first casing 24 of the radial contraction and expansion ring 2 by measuring the deformation parameter of the rubber diaphragm, and then calculate the corresponding radial volume change parameter of the well cement ring according to the deformation parameter of the first casing 24.

In one embodiment, a rubber seal is achieved between the radial contraction and expansion ring 2 and the upper cover 21 as well as between the radial contraction and expansion ring 2 and the lower cover 22 respectively, which can prevent the leakage of the cement injected into the annulus between the first casing 23 and the second casing 24, so as to more accurately test and obtain the radial volume change parameter. Of course, it should be noted that the seal of the gap between the radial contraction and expansion ring 2 and the upper cover 21 as well as between the radial contraction and expansion ring 2 and the lower cover 22 by using the rubber as listed above are only for better describing the embodiments of the present application. During implementation, other appropriate material may also be selected as the sealing material.

In one embodiment, during implementation, an injection hole and a discharge hole may be provided on the upper cover 21, wherein the injection hole and the discharge hole are respectively communicated with the annulus between the first casing 23 and the second casing 24. Thus, during implementation, the cement slurry to be determined may be injected into the annulus through the injection hole, and original air in the annulus may be discharged through the discharge hole while the cement slurry is injected into the annulus. When the cement slurry begins to overflow from the discharge hole, it can be determined that the annulus has been fully injected with the cement slurry, and at that time, the injection of the cement slurry into the injection hole can be stopped.

In one embodiment, during implementation, the upper cover 21 and the lower cover 22 may be provided with a pressure adjusting hole, respectively, wherein the pressure adjusting hole may be communicated with an interior of the second casing 24. Thus, during implementation, air may be injected into an inner space of the second casing 24 through the pressure adjusting hole based on the test requirement, so as to adjust the pressure in the second casing 24, and accurately simulate the influence on the well cement ring from the pressure in the downhole casing under an actual construction environment.

In one embodiment, during implementation, the upper cover 21 and the lower cover 22 may be provided with two pressure adjusting holes, respectively, so as to adjust the internal pressure of the second casing 24. Of course, it should be noted that the number of the pressure adjusting holes listed above is only a schematic illustration. During implementation, any other number of pressure adjusting holes may also be provided based on the specific condition, which is not limited herein.

In one embodiment, during implementation, a fixing hole may be provided at a center position of the lower cover 22, wherein the fixing hole specifically may be used to fix the radial contraction and expansion ring 2 in the reaction kettle 1; wherein an inner side of the fixing hole may be provided with a thread, and the bottom of the reaction kettle 1 may be provided with a fixing screw having a thread corresponding to the thread of the fixing hole. Thus, the radial contraction and expansion ring 2 can be fixed in the reaction kettle 1 by screwing the fixing screw into the fixing hole.

In one embodiment, the apparatus specifically may further include a processor, wherein the processor specifically may be connected to the volume change parameter tester 5, and used to determine the volume stability of the well cement according to the radial volume change parameter and the axial volume change parameter, wherein the axial volume change parameter is measured by the apparatus for determining the volume stability of the well cement without the radial contraction and expansion ring.

In this embodiment, the above apparatus specifically may be an electronic device having certain data processing and analysis capability, such as a notebook computer, a desktop computer, a server, or the like, which is not limited herein.

In one embodiment, it should be noted that the apparatus for determining the volume stability of the well cement without the radial contraction and expansion ring is similar to the device for testing the axial volume change parameter of the cement in the existing method. Therefore, during implementation, the well cement to be determined may be directly injected into the reaction kettle 1, the preset temperature and the preset pressure are respectively provided by the heater 3 and the pressurizer 4 to simulate the temperature and pressure environment for the cement ring under actual conditions, and a corresponding axial volume change parameter of the well cement is measured by the volume change parameter tester 5.

In one embodiment, during implementation, the apparatus for determining the volume stability of the well cement may be used to determine the stabilities of various cements of different ratios (e.g., No. 1 cement, No. 2 cement and No. 3 cement) respectively to select a satisfactory cement for cementing construction. Next, an example of determining a volume stability of No. 1 cement is given to describe how to determine the volume stability of No. 1 cement using the above apparatus. No. 1 cement slurry is injected into the annulus between the first casing 23 and the second casing 24 of the radial contraction and expansion ring 2 through the injection hole, until the cement slurry starts to overflow from the discharge hole. The radial contraction and expansion ring 2 in the reaction kettle 1 is heated and pressurized by the heater 3 and the pressurizer 4, and the temperature in the reaction kettle 1 is maintained at the preset temperature and the pressure in the reaction kettle 1 is maintained at the preset pressure, so as to simulate the temperature and pressure environment for the downhole cement ring in the actual construction process. Meanwhile, the pressure in the second casing 24 may be adjusted through the pressure adjusting hole based on the test requirement, so as to more realistically simulate the internal pressure of the second casing 24 under actual conditions. The volume change parameter tester 5 is employed to test the deformation parameter of the rubber diaphragm of the reaction kettle 1, so as to obtain a deformation parameter of the first casing 23, such that a radial volume change parameter of No. 1 cement can be calculated according to the deformation parameter of the first casing 23, thereby completing the determination of the radial volume change parameter of No. 1 cement. Next, the radial contraction and expansion ring 2 is taken out, and the reaction kettle 1 is fully injected with No. 1 cement slurry. Similarly, the radial contraction and expansion ring 2 in the reaction kettle 1 is heated and pressurized by the heater 3 and the pressurizer 4, and the temperature in the reaction kettle 1 is maintained at the preset temperature and the pressure in the reaction kettle 1 is maintained at the preset pressure. Next, the deformation parameter of the rubber diaphragm is tested by the volume change parameter tester 5, and thus a corresponding axial volume change parameter of No. 1 cement can be calculated according to the deformation parameter of the rubber diaphragm. The overall stability of No. 1 cement is comprehensively evaluated with the axial volume change parameter and the radial volume change parameter of No. 1 cement, so as to finally determine the stability of No. 1 cement. In the same way, the stabilities of No. 2 cement and No. 3 cement are determined, respectively. The stabilities of No. 1 to No. 3 cements are compared with each other, and the cement with a stability satisfying the construction requirement is selected for cementing construction.

As can be seen from the above description, the apparatus for determining the volume stability of the well cement provided by the embodiments of the present application comprehensively evaluate the volume stability of the well cement by detecting a radial volume change parameter of the well cement by means of the disposed radial contraction and expansion ring so as to introduce the radial volume change parameter of the well cement in consideration of the actual volume change characteristics of the downhole cement ring, thereby solving the technical problem of the existing methods that the determination of the volume stability of the well cement is not comprehensive and the accuracy thereof is poor, and achieving the technical effect of more accurately and comprehensively evaluating the volume stability of the well cement by detecting and utilizing the radial volume change parameter of the well cement. The above apparatus takes the rubber casing as the first casing to simulate the formation and takes the steel casing as the second casing to simulate the downhole casing further in consideration of the actual downhole environment characteristics of the well cement ring. In addition, since the first casing is a rubber casing with a good elasticity, the radial volume change parameter of the well cement can be represented by detecting the deformation parameter of the first casing, thereby increasing the accuracy of the determined radial volume change parameter of the well cement. Moreover, the above apparatus provides the preset temperature and the preset pressure by using the heater and the pressurizer to more accurately simulate the temperature environment and the pressure environment of the downhole well cement ring, thereby further increasing the accuracy of the determined radial volume change parameter.

Figure 2:
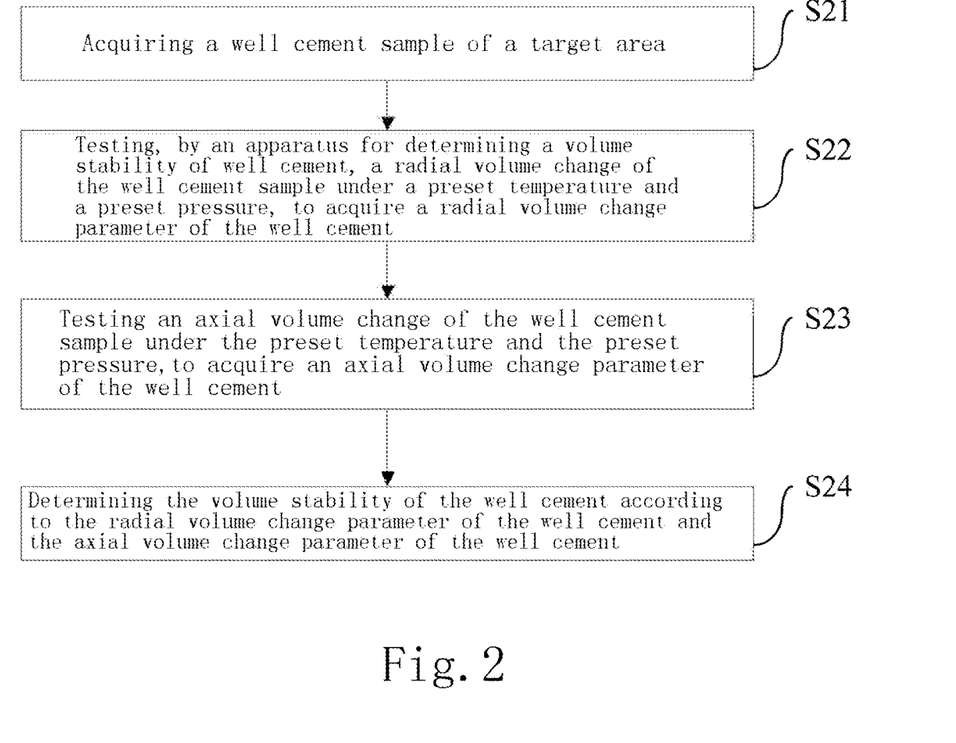
FIG. 2 is a processing flow diagram of a method for determining a volume stability of well cement provided by an embodiment of the present application.

According to the apparatus for determining the volume stability of the well cement, referring to a processing flow diagram of a method for determining a volume stability of well cement provided by an embodiment of the present application as illustrated in FIG. 2, the embodiments of the present application further provide a method for determining a volume stability of well cement. During implementation, the method may include S21: acquiring a well cement sample of a target area; S22: testing, by an apparatus for determining a volume stability of well cement, a radial volume change of the well cement sample under a preset temperature and a preset pressure, to acquire a radial volume change parameter of the well cement; S23: testing an axial volume change of the well cement sample under the preset temperature and the preset pressure, to acquire an axial volume change parameter of the well cement; and S24: determining the volume stability of the well cement according to the radial volume change parameter of the well cement and the axial volume change parameter of the well cement.

In one embodiment, the well cement sample specifically may include various cements of different ratios for constructing a cement ring between a downhole formation and a downhole casing in the target area. In this way, a cement having the best stability under the environment of the target area may be selected from the various cements of different ratios to perform a cementing construction in the target area, i.e., to construct the cement ring between the downhole formation and the downhole casing in the target area.

In one embodiment, the preset temperature specifically may be determined according to a downhole temperature of the target area, and the preset pressure specifically may be determined according to a downhole pressure of the target area.

In one embodiment, during implementation, 'testing, by the apparatus for determining the volume stability of well cement, the radial volume change of the well cement sample under the preset temperature and a preset pressure, to acquire the radial volume change parameter of the well cement' specifically may include fully injecting the well cement sample into an annulus between a first casing and a second casing of a radial contraction and expansion ring, to form a well cement ring; heating and pressurizing by a heater and a pressurizer, to reach and maintain an environment condition of the preset temperature and the preset pressure; measuring, by a volume change parameter tester, a deformation parameter of the first casing under the environment condition, and calculating a radial volume change parameter of the well cement sample according to the deformation parameter of the first casing.

In one embodiment, during implementation, 'testing the axial volume change of the well cement sample under the preset temperature and the preset pressure, to acquire the axial volume change parameter of the well cement' may include taking out the radial contraction and expansion ring from the apparatus for determining the volume stability of the well cement, and injecting the well cement sample into a reaction kettle; heating and pressurizing by the heater and the pressurizer, to reach and maintain an environment condition of the preset temperature and the preset pressure; measuring, by the volume change parameter tester, the axial volume change parameter of the well cement sample under the environment condition.

In one embodiment, during implementation, 'determining the volume stability of the well cement according to the radial volume change parameter of the well cement and the axial volume change parameter of the well cement' may include S1: comparing the radial volume change parameter with a radial volume change threshold; and comparing the axial volume change parameter with an axial volume change threshold; S2: determining that the volume stability of the well cement is satisfactory, when the radial volume change parameter is smaller than the radial volume change threshold and the axial volume change parameter is smaller than the axial volume change threshold.

In one embodiment, the value of the radial volume change threshold specifically may be set as 2%, and the value of the axial volume change threshold specifically may be set as 3%. Of course, it should be noted that the values listed above are only for better describing the embodiments of the present application. During implementation, other appropriate values may also be selected as the radial volume change threshold and the axial volume change threshold according to the specific conditions and the construction accuracy requirement, which are not limited herein.

The individual embodiments herein are described in a progressive manner, and the same or similar portions of the individual embodiments can refer to each other. Each embodiment lays an emphasis on its distinctions from other embodiments. In particular, the system embodiment is simply described since it is substantially similar to the method embodiment, and please refer to the description of the method embodiment for the relevant content.

It should be noted that any system, apparatus, module or unit set forth in the above embodiments specifically may be implemented by a computer chip or an entity, or by a product having a certain function. For the convenience of description, herein the apparatus is described by being divided into various units based on its functions and described respectively. Of course, the functions of the various units may be realized in the same one or more software and/or hardware when the present application is implemented.

In addition, in the specification, the adjectives such as first and second may be only used to distinguish one element or action from another element or action, without requiring or implying any such relationship or order. Where circumstances permit, the reference to an element, or a component, or a step (and the like) should not be construed as being limited to only one element, one component or one step, but may concern one or more thereof.

As can be seen from the above description, the method for determining the volume stability of the well cement provided by the embodiments of the present application comprehensively evaluate the volume stability of the cement by detecting a radial volume change parameter of the well cement utilizing the radial contraction and expansion ring so as to introduce the radial volume change parameter of the well cement in consideration of the actual volume change characteristics of the downhole cement ring, thereby solving the technical problem of the existing methods that the determination of the volume stability of the well cement is not comprehensive and the accuracy thereof is poor, and achieving the technical effect of more accurately and comprehensively evaluating the volume stability of the well cement by detecting and utilizing the radial volume change parameter of the well cement. The above apparatus takes the rubber casing as the first casing and takes the steel casing as the second casing further in consideration of the actual downhole environment of the cement ring. Since a rubber casing has a good elasticity, the radial volume change parameter of the well cement can be represented by detecting the deformation parameter of the first casing, thereby increasing the accuracy of the determined radial volume change parameter of the well cement. Moreover, the above apparatus provides the preset temperature and the preset pressure by using the heater and the pressurizer to more accurately simulate the temperature environment and the pressure environment of the downhole cement ring, thereby further increasing the accuracy of the determined radial volume change parameter of the well cement.

Figure 3:
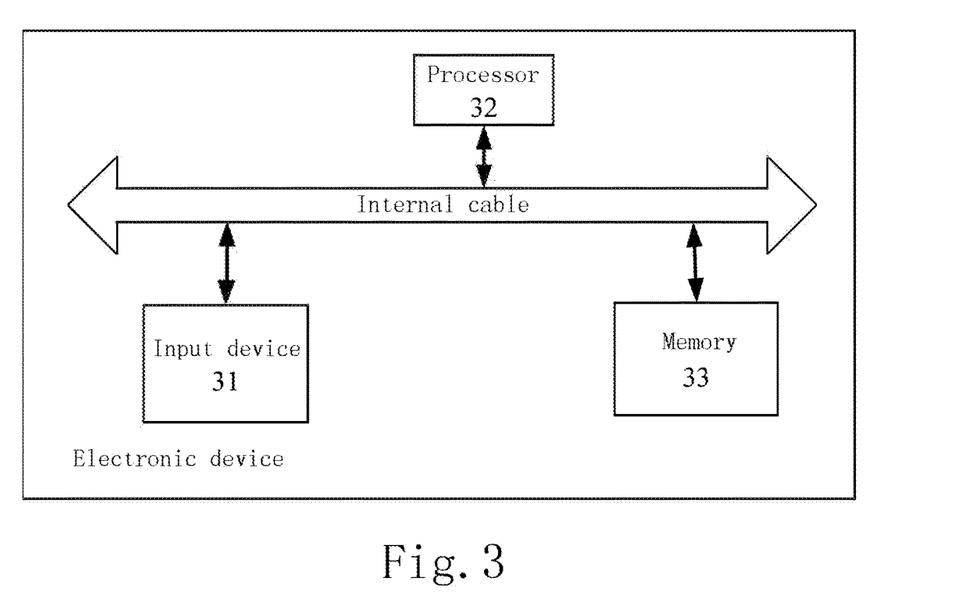
FIG. 3 is a schematic structural diagram of an electronic device based on a method for determining a volume stability of well cement provided by an embodiment of the present application.

The embodiments of the present application further provide an electronic device. For the detail, please refer to FIG. 3, which illustrates a schematic structural diagram of an electronic device based on a method for determining a volume stability of well cement provided by an embodiment of the present application. The electronic device specifically may include an input device 31, a processor 32 and a memory 33. In which, the input device 31 specifically may be used to input a well cement sample of a target area. The processor 32 specifically may be used to, by an apparatus for determining a volume stability of well cement, test a radial volume change of the well cement sample under a preset temperature and a preset pressure to obtain a radial volume change parameter; test an axial volume change of the well cement sample under the preset temperature and the preset pressure to obtain an axial volume change parameter; and determine the volume stability of the well cement according to the radial volume change parameter and the axial volume change parameter. The memory 33 specifically may be used to store intermediate data such as the radial volume change parameter and the axial volume change parameter.

In this embodiment, the input device specifically may be one of the main devices for information exchange between a user and a computer system. The input device may include a keyboard, a mouse, a camera, a scanner, a light pen, a handwriting input board, a voice input device, etc.; and the input device is used to input raw data and a program that processes these data into a computer. The input device may also acquire and receive data transmitted from other modules, units and devices. The processor may be implemented in any suitable manner. For example, the processor may take the form of, for example, a microprocessor, a processor, a computer readable medium storing computer readable program codes (e.g. software or firmware) executable by the (micro)processor, a logic gate, a switch, an Application Specific Integrated Circuit (ASIC), a programmable logic controller, or an embedded microcontroller or the like. The memory specifically may be a memory device for saving information in the modern information technologies. The memory may include several hierarchies: in the digital system, any means capable of saving binary data may be a memory; in the integrated circuit, any circuit that has no physical form but has a storage function also may be referred to as a memory, such as a RAM, a FIFO, etc.; and in the system, any storage means that has a physical form also may be a memory, such as a memory stick, a TF card, etc.

In this embodiment, the functions and effects specifically realized by the electronic device may be explained with reference to other embodiments, and the details are omitted herein.

The embodiments of the present application further provide a computer storage medium based on a method for determining a volume stability of well cement, and the computer storage medium is stored with computer program instructions which, when being executed, perform the operations of: acquiring a well cement sample of a target area; testing, by an apparatus for determining a volume stability of well cement, a radial volume change of the well cement sample under a preset temperature and a preset pressure to acquire a radial volume change parameter; testing an axial volume change of the well cement sample under the preset temperature and the preset pressure to acquire an axial volume change parameter; and determining the volume stability of the well cement according to the radial volume change parameter and the axial volume change parameter.

In this embodiment, the storage medium may include, but not limited to, a Random Access Memory (RAM), a Read-Only Memory (ROM), a cache, a Hard Disk Drive (HDD) or a memory card. The memory may be used to store the computer program instructions. The network communication unit may be an interface provided in accordance with a standard stipulated by a communication protocol and used for network connection and communication.

In this embodiment, the functions and effects specifically realized by the program instructions stored in the computer storage medium may be explained with reference to other embodiments, and the details are omitted herein.

In an example of an implementation scene, the apparatus and method for determining the volume stability of the well cement provided by the embodiments of the present application are applied to evaluate the radial stability of a cement ring for cementing construction in a target area (i.e., to determine the radial volume change parameter), so as to determine whether the used cement satisfies the construction requirement. The implementation process may refer to the following content.

In this embodiment, the stabilities of the following cements need to be evaluated: No. 1 cement (which belonging to a flexible cement slurry system with a large temperature difference and a density of 1.90 g/cm$^3$) for 7-cun drilling liner cementation of a gas well X1, and No. 2 cement slurry (which belonging to a self-healing cement slurry system with a density of 1.90 g/cm$^3$) for 7-cun drilling liner cementation of a well gas X2 in a target area. The samples of the two types of cements are acquired, respectively. In which, the samples of the above cement specifically may refer to cement slurries of the same configuration. During implementation, the two types of cement slurries may be configured according to an API standard, respectively.

In this embodiment, during implementation, the apparatus for determining the volume stability of the well cement provided by the embodiments of the present application may be employed to inject two types of cement samples (the cement slurry of No. 1 cement and the cement slurry of No. 2 cement) into two radial contraction and expansion rings through the injection holes, respectively, until the cements overflow from the discharge holes; fix the two radial contraction and expansion rings fully injected with the cements into two reaction kettles, respectively; heat and pressurize the radial contraction and expansion rings in the two reaction kettles to the preset temperature and the preset pressure by the heater and the pressurizer, respectively; and at the same time, measure the radial volume change parameters of the two types of cements under the preset temperature and the preset pressure in real time by the volume change parameter tester.

Figure 4:
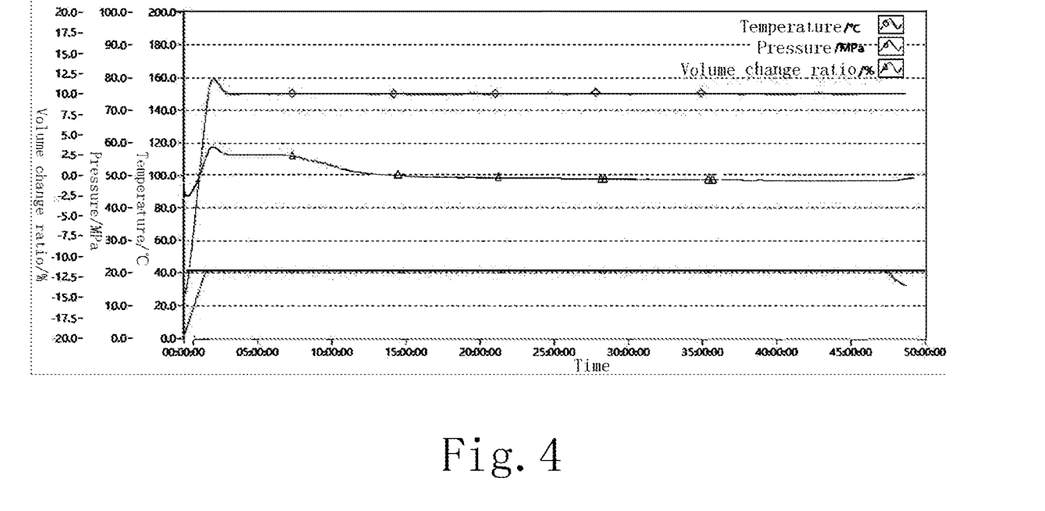
FIG. 4 is a schematic diagram of a radial volume change parameter, under the condition of 21 MPa and 150° C., of No. 1 cement obtained by applying an apparatus and method for determining a volume stability of well cement provided by embodiments of the present application to a scene example.
Figure 5:
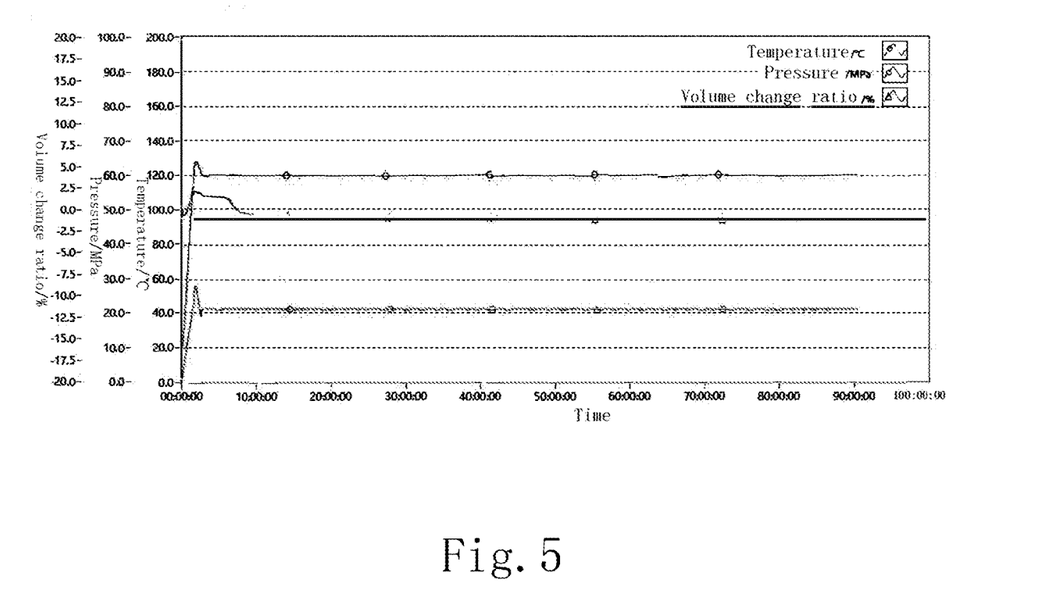
FIG. 5 is a schematic diagram of a radial volume change parameter, under the condition of 21 MPa and 120° C., of No. 1 cement obtained by applying an apparatus and method for determining a volume stability of well cement provided by embodiments of the present application to a scene example.
Figure 6:
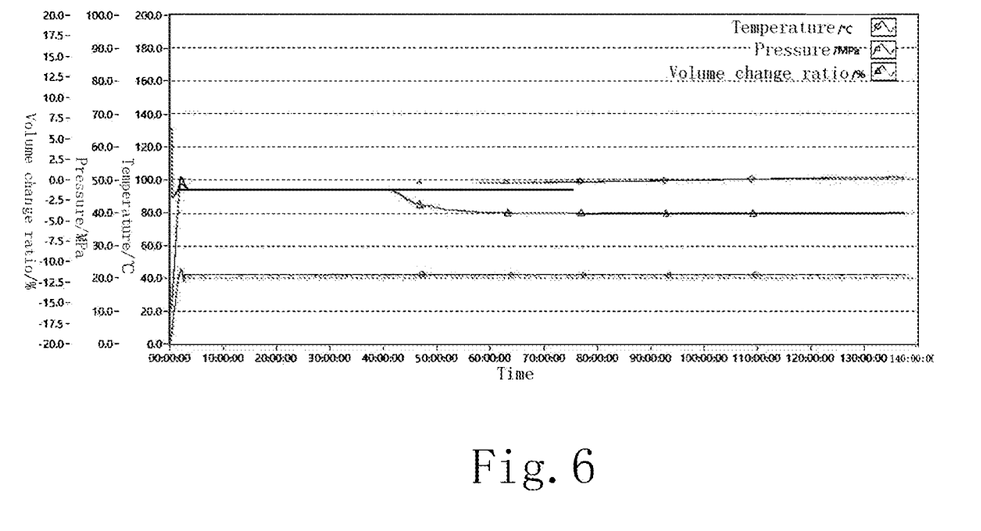
FIG. 6 is a schematic diagram of a radial volume change parameter, under the condition of 21 MPa and 95° C., of No. 1 cement obtained by applying an apparatus and method for determining a volume stability of well cement provided by embodiments of the present application to a scene example.
Figure 7:
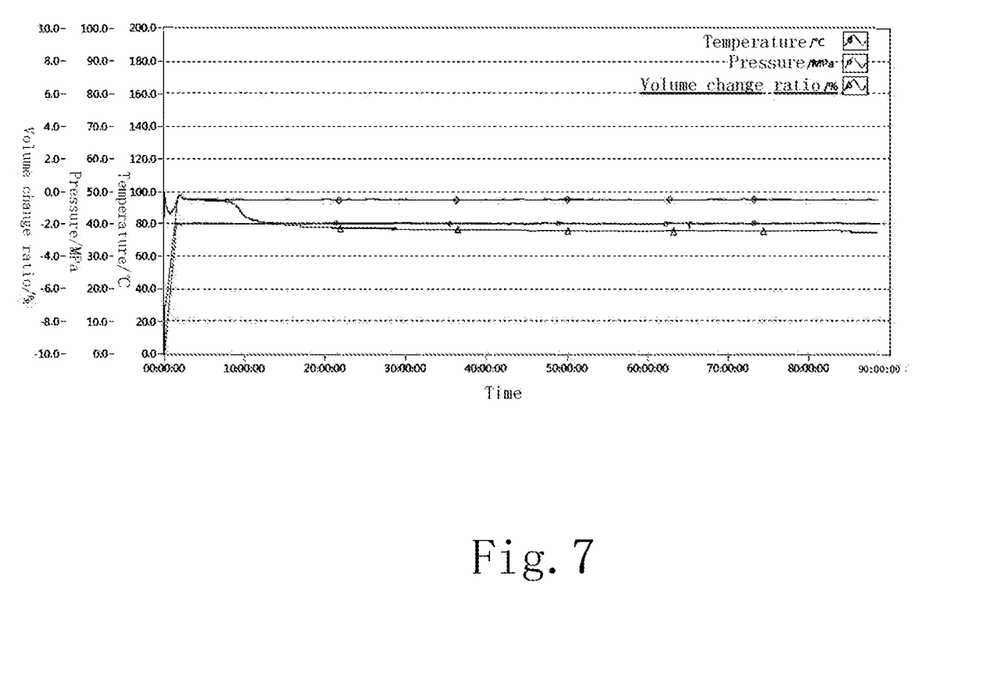
FIG. 7 is a schematic diagram of a radial volume change parameter, under the condition of 40 MPa and 95° C., of No. 2 cement obtained by applying an apparatus and method for determining a volume stability of well cement provided by embodiments of the present application to a scene example.
Figure 8:
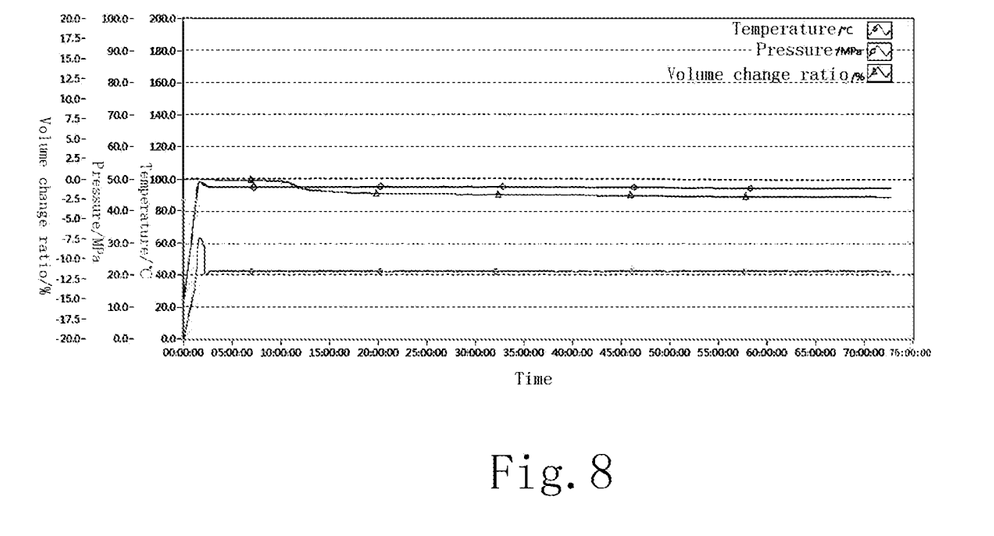
FIG. 8 is a schematic diagram of a radial volume change parameter, under the condition of 21 MPa and 95° C., of No. 2 cement obtained by applying an apparatus and method for determining a volume stability of well cement provided by embodiments of the present application to a scene example.
Figure 9:
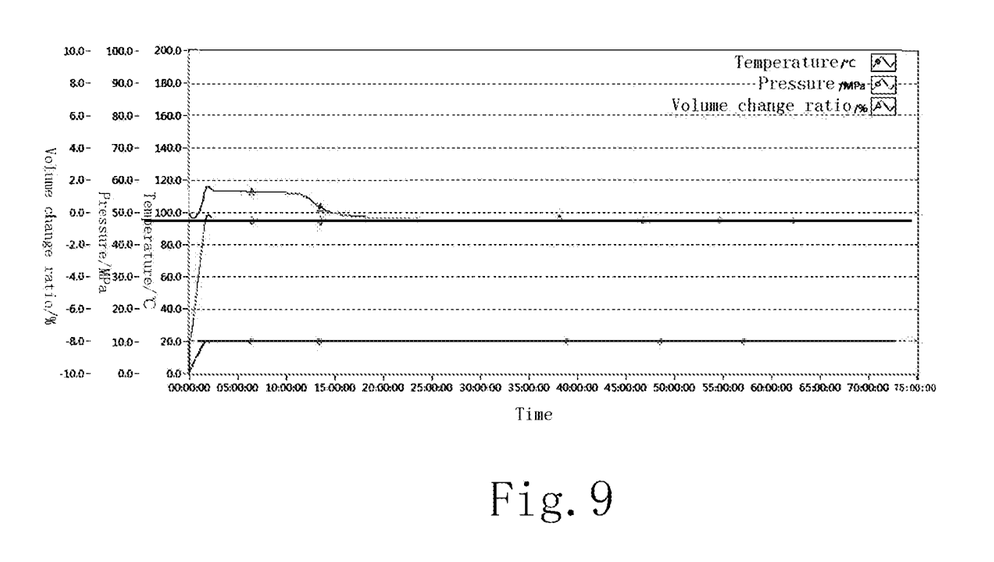
FIG. 9 is a schematic diagram of a radial volume change parameter, under the condition of 10 MPa and 95° C., of No. 2 cement obtained by applying an apparatus and method for determining a volume stability of well cement provided by embodiments of the present application to a scene example.

In this embodiment, with respect to different downhole environments in which the two types of cements are applied, a plurality of groups of preset temperatures and preset pressures may be set correspondingly for the test. Specifically, regarding No. 1 cement, in order to evaluate the radial volume stabilities at different temperatures, a preset pressure may be set as 21 MPa, and a plurality of groups of different preset temperatures may be set as 150° C., 120° C. and 95° C., respectively, so as to test the radial volume change parameters corresponding to different preset temperatures at the preset pressure of 21 MPa. Specifically, please refer to FIG. 4 which illustrates a schematic diagram of a radial volume change parameter, under the condition of 21 MPa and 150° C., of No. 1 cement obtained by applying an apparatus and method for determining a volume stability of well cement provided by the embodiments of the present application to a scene example, FIG. 5 which illustrates a schematic diagram of a radial volume change parameter, under the condition of 21 MPa and 120° C., of No. 1 cement obtained by applying an apparatus and method for determining a volume stability of well cement provided by the embodiments of the present application to a scene example, and FIG. 6 which illustrates a schematic diagram of a radial volume change parameter, under the condition of 21 MPa and 95° C., of No. 1 cement obtained by applying an apparatus and method for determining a volume stability of well cement provided by embodiments of the present application to a scene example. As can be seen from the analyses, No. 1 cement has a radial volume change parameter of 1.82% when the preset pressure is 21 MPa and the preset temperature is 150° C., a radial volume change parameter of −0.5% when the preset pressure is 21 MPa and the preset temperature is 120° C., and a radial volume change parameter of −3.46% when the preset pressure is 21 MPa and the preset temperature is 95° C. Regarding No. 2 cement, in order to evaluate the radial volume stabilities at different pressures, a preset temperature may be set as 95° C., and a plurality of groups of different preset pressures may be set as 40 MPa, 21 Mpa and 10 Mpa, respectively, so as to test the radial volume change parameters corresponding to different preset pressures at the preset temperature of 95° C. Specifically, please refer to FIG. 7 which illustrates a schematic diagram of a radial volume change parameter, under the condition of 40 MPa and 95° C., of No. 2 cement obtained by applying an apparatus and method for determining a volume stability of well cement provided by embodiments of the present application to a scene example, FIG. 8 which illustrates a schematic diagram of a radial volume change parameter, under the condition of 21 MPa and 95° C., of No. 2 cement obtained by applying an apparatus and method for determining a volume stability of well cement provided by embodiments of the present application to a scene example, and FIG. 9 which illustrates a schematic diagram of a radial volume change parameter, under the condition of 10 MPa and 95° C., of No. 2 cement obtained by applying an apparatus and method for determining a volume stability of well cement provided by embodiments of the present application to a scene example. As can be seen from the analyses, No. 2 cement has a radial volume change parameter of −1.16% when the preset pressure is 40 MPa and the preset temperature is 95° C., a radial volume change parameter of −0.16% when the preset pressure is 21 MPa and the preset temperature is 95° C., and a radial volume change parameter of 0.17% when the preset pressure is 10 MPa and the preset temperature is 95° C.

The apparatus and method for determining the volume stability of the well cement provided by the embodiments of the present application are verified through the above scene examples; because they comprehensively evaluate the volume stability of the well cement by detecting a radial volume change parameter of the well cement by means of the disposed radial contraction and expansion ring so as to introduce the radial volume change parameter of the well cement in consideration of the actual volume change characteristics of the downhole cement, they solve the technical problem of the existing methods that the determination of the volume stability of the well cement is not comprehensive and the accuracy thereof is poor, and achieve the technical effect of more accurately and comprehensively evaluating the volume stability of the well cement by detecting and utilizing the radial volume change parameter of the well cement.

Although mentioning different embodiments, the present application is not limited to the industry standards, the situations described in the embodiments or the like. Some industry standards, customized implementation solutions, or implementation solutions slightly amended based on those described in the embodiments can also achieve the same, equivalent or similar implementation effects of the above embodiments or implementation effects predictable after modification. The embodiments applying the manners of data acquisition, processing, output, judgement, etc. after amendment or modification still fall within the range of the optional implementation solutions of the present application.

Although the present application provides the method operation steps as described in the embodiments or the flowcharts, more or less operation steps may be included based on the conventional or non-creative means. The order of the steps listed in the embodiments is merely one of various execution orders of the steps, rather than a unique execution order. At an actual device or client product, the steps may be performed in sequence or in parallel according to the methods illustrated in the embodiments or drawings (e.g., by a parallel processor or under a multi-threaded processing environment and even a distributed data processing environment). The term "comprise", "include" or any other variant intends to cover the non-exclusive inclusions, so that a process, a method, a commodity or a device comprising a series of elements comprise not only those elements, but also other elements not explicitly listed, or further comprise inherent elements of such process, method, commodity or device. In a case where there is no further limitation, it does not exclude other identical elements existing in the process, method, commodity or device comprising the elements.

Any apparatus, module or the like set forth in the embodiments specifically may be implemented by a computer chip or an entity, or by a product having a certain function. For the convenience of description, herein the apparatus is described by being divided into various modules based on its functions and described respectively. Of course, when the present application is implemented, the functions of the various modules may be realized in the same one or more software and/or hardware, or a module that realizes a function may be implemented by a combination of a plurality of submodules. The apparatus embodiments described above are merely illustrative. For instance, the division of the module is only a logical function division, and there may be other division manners during actual implementation, e.g., a plurality of modules or components may be combined or integrated into another system, or some features may be omitted or not implemented.

As also known to those skilled in the art, in addition to implementing the controller merely with the computer readable program codes, it is completely possible to logically program the methodical steps to enable the controller to realize the same function in the form such as a logic gate, a switch, an application-specific integrated circuit, a programmable logic controller, or an embedded microcontroller. Thus, the controller may be considered as a hardware component, while means included therein for realizing various functions may also be regarded as structures within the hardware component. Or, the means for realizing various functions even may be regarded as either software modules that can implement the method or structures within the hardware component.

The present application may be described in the general context of computer executable instructions executed by the computer, e.g., the program module. In general, the program module includes routine, program, object, component, data structure, etc. executing a particular task or realizing a particular abstract data type. The present application may also be put into practice in the distributed computing environments where tasks are executed by remote processing devices connected through a communication network. In the distributed computing environments, the program modules may be located in the local and remote computer storage medium including the storage device.

As can be seen from the descriptions of the above embodiments, those skilled in the art can clearly understand that the present application can be implemented by means of software plus a necessary universal hardware platform. Based on this understanding, the essence of the technical solution of the present disclosure or the part making a contribution to the prior art can be embodied in the form of a computer software product, which may be stored in a storage medium, such as a ROM/RAM, a magnetic disk, an optical disk, etc., and include several instructions to enable a computer device (a personal computer, a server, a network device, etc.) to carry out the embodiments of the present disclosure, or methods described in some parts of the embodiments.

The embodiments herein are all described in a progressive manner, and the same or similar portions of the embodiments can refer to each other. Each embodiment lays an emphasis on its distinctions from other embodiments. The present application may be used in a variety of general or dedicated computer system environments or configurations, such as a personal computer, a server computer, a handheld or portable device, a tablet device, a multiprocessor system, a microprocessor-based system, a set-top box, a programmable electronic device, a network PC, a small-scale computer, a large-scale computer, a distributed computing environment including any of the above systems or devices, and the like.

Although the present application is described through the embodiments, those skilled in the art will know that that there are many modifications and changes of the present application without deviating from the spirit of the present application, and it is intended that the appended implementations include those modifications and changes without deviating from the spirit of the present application.

What is claimed is:

1. An apparatus for determining a volume change of well cement, comprising:
    a reaction kettle, a radial contraction and expansion ring, a heater, a pressurizer, and a volume change parameter tester, wherein:
    the radial contraction and expansion ring comprises a first casing and a second casing, the first casing is a casing made of elastic material, the second casing is a steel casing, the first casing sheathes the second casing, an upper cover and a lower cover are provided at a top and a bottom of the radial contraction and expansion ring, respectively, and an annulus between the first casing and the second casing is used for accommodate a well cement sample of a target area to be detected;
    the radial contraction and expansion ring is provided in the reaction kettle;
    the heater is connected to the reaction kettle, and is used to provide a preset temperature to the radial contraction and expansion ring; the pressurizer is connected to the reaction kettle, and is used to provide a preset pressure to the radial contraction and expansion ring; and the volume change parameter tester is connected to the reaction kettle, and is used to determine a radial volume change parameter of the well cement by detecting a deformation parameter of the second casing under a condition of the preset temperature and the preset pressure, the radial volume change parameter is used to determine the volume change of the well cement, wherein the upper cover and the lower cover are used to make an axial volume of the well cement unable to change.

2. The apparatus according to claim 1, wherein a rubber seal is achieved between the radial contraction and expansion ring and the upper cover, and a rubber seal is achieved between the radial contraction and expansion ring and the lower cover.

3. The apparatus according to claim 1, wherein an injection hole and a discharge hole are provided on the upper cover, the injection hole is communicated with the annulus between the first casing and the second casing, and the discharge hole is communicated with the annulus between the first casing and the second casing.

4. The apparatus according to claim 1, wherein a pressure adjusting hole is provided on the upper cover and the lower cover, respectively, and is communicated with an interior of the second casing.

5. The apparatus according to claim 1, wherein a fixing hole is provided at a center position of the lower cover, and is used to fix the radial contraction and expansion ring in the reaction kettle.

6. The apparatus according to claim 1, further comprising a processor connected to the volume change parameter tester and used to determine the volume change of the well cement according to the radial volume change parameter of the well cement and an axial volume change parameter of the well cement, the axial volume change parameter of the well cement represents an axial volume change rate of the well cement.

7. A method for determining a volume change of well cement, comprising:
acquiring a well cement sample of a target area;
testing a radial volume change of the well cement sample under a condition of a preset temperature and a preset pressure to acquire a radial volume change parameter of the well cement by an apparatus, the apparatus comprising:
a reaction kettle, a radial contraction and expansion ring, a heater, a pressurizer, and a volume change parameter tester, wherein:
the radial contraction and expansion ring comprises a first casing and a second casing, the first casing is a casing made of elastic material, the second casing is a steel casing, the first casing sheathes the second casing, an upper cover and a lower cover are provided at a top and a bottom of the radial contraction and expansion ring, respectively, and an annulus between the first casing and the second casing is used for accommodate a well cement sample of a target area to be detected;
the radial contraction and expansion ring is provided in the reaction kettle;
the heater is connected to the reaction kettle, and is used to provide a preset temperature to the radial contraction and expansion ring; the pressurizer is connected to the reaction kettle, and is used to provide a preset pressure to the radial contraction and expansion ring; and
the volume change parameter tester is connected to the reaction kettle, and is used to determine a radial volume change parameter of the well cement by detecting a deformation parameter of the second casing under a condition of the preset temperature and the preset pressure, the radial volume change parameter is used to determine the volume change of the well cement;
wherein the upper cover and the lower cover are used to make an axial volume of the well cement unable to change;
testing an axial volume change of the well cement sample under the condition of the preset temperature and the preset pressure, to acquire an axial volume change parameter of the well cement; and
determining the volume change of the well cement according to the radial volume change parameter of the well cement and the axial volume change parameter of the well cement.

8. The method according to claim 7, wherein the preset temperature is determined according to a downhole temperature of the target area, and the preset pressure is determined according to a downhole pressure of the target area.

9. The method according to claim 7, wherein determining the volume change of the well cement according to the radial volume change parameter of the well cement and the axial volume change parameter of the well cement comprises:
comparing the radial volume change parameter of the well cement with a radial volume change threshold, and comparing the axial volume change parameter of the well cement with an axial volume change threshold; and
when the radial volume change parameter of the well cement is smaller than the radial volume change threshold and the axial volume change parameter of the well cement is smaller than the axial volume change threshold, determining that the volume change of the well cement is satisfactory.

10. The method according to claim 7, wherein the well cement sample comprises cements of a plurality of ratios for constructing a cement ring between a downhole formation and a downhole casing in the target area.

* * * * *